(12) United States Patent
Napoli

(10) Patent No.: US 7,456,393 B2
(45) Date of Patent: Nov. 25, 2008

(54) DEVICE FOR TESTING SURFACES OF ARTICLES FOR TRACES OF EXPLOSIVES AND/OR DRUGS

(75) Inventor: Joseph D. Napoli, Windham, NH (US)

(73) Assignee: GE Homeland Protection, Inc., Newark, CA (US)

( * ) Notice: Subject to any disclaimer, the term of this patent is extended or adjusted under 35 U.S.C. 154(b) by 664 days.

(21) Appl. No.: 10/774,003

(22) Filed: Feb. 6, 2004

(65) Prior Publication Data
US 2005/0019220 A1    Jan. 27, 2005

Related U.S. Application Data

(60) Provisional application No. 60/462,559, filed on Apr. 10, 2003.

(51) Int. Cl.
*G01N 1/04* (2006.01)

(52) U.S. Cl. ............... 250/288; 73/864; 73/864.71; 378/186; 378/88; 378/86; 250/287; 250/286

(58) Field of Classification Search .............. 250/288; 73/864.81; 422/99
See application file for complete search history.

(56) References Cited

U.S. PATENT DOCUMENTS

| | | | |
|---|---|---|---|
| 4,045,997 A | 9/1977 | Showalter et al. | |
| 4,202,200 A | 5/1980 | Ellson | |
| 4,772,794 A | 9/1988 | Jenkins | |
| 4,781,972 A | 11/1988 | Sakane et al. | |
| 4,896,547 A | 1/1990 | Arney et al. | |
| 4,964,309 A | 10/1990 | Jenkins | |
| 4,987,767 A | 1/1991 | Corrigan et al. | |
| 5,027,643 A | 7/1991 | Jenkins | |
| 5,109,691 A | 5/1992 | Corrigan et al. | |
| 5,200,614 A | 4/1993 | Jenkins | |
| 5,380,997 A * | 1/1995 | Hania et al. | ........... 235/485 |
| 5,405,781 A | 4/1995 | Davies et al. | |
| 5,491,337 A | 2/1996 | Jenkins et al. | |
| 5,585,575 A | 12/1996 | Corrigan et al. | |
| 5,741,984 A | 4/1998 | Danylewych-May et al. | |
| 5,753,832 A | 5/1998 | Bromberg et al. | |
| 5,760,314 A | 6/1998 | Bromberg et al. | |
| 5,859,362 A | 1/1999 | Neudorfl et al. | |
| 5,859,375 A | 1/1999 | Danylewych-May et al. | |
| 5,915,268 A | 6/1999 | Linker et al. | |
| 6,073,499 A | 6/2000 | Settles | |
| 6,334,365 B1 | 1/2002 | Linker et al. | |
| 6,375,697 B2 | 4/2002 | Davies | |

(Continued)

FOREIGN PATENT DOCUMENTS

EP    0 247 243    12/1987

*Primary Examiner*—Jack I. Berman
*Assistant Examiner*—Andrew Smyth
(74) *Attorney, Agent, or Firm*—Global Patent Operation (57) ABSTRACT

A device is provided for testing surfaces of a card for the presence of explosives, drugs or other substances of interest. The device includes a slot for receiving the card. Thin metallic wiper blades are dispose in alignment with the slot and wipe over surfaces of the card as the card is passed through the slot. Thus, substances on the surface of the card are transferred to the wiper blade. The wiper blade then is enclosed and rapidly heated to desorb the material retrieved from the card. The enclosure then is placed in communication with a detector to test for the presence of substances of interest.

21 Claims, 7 Drawing Sheets

U.S. PATENT DOCUMENTS

| | | |
|---|---|---|
| 6,407,382 B1 | 6/2002 | Spangler |
| 6,575,553 B1 * | 6/2003 | Williams et al. ............... 347/22 |
| 6,610,977 B2 * | 8/2003 | Megerle ..................... 250/287 |
| 6,642,513 B1 | 11/2003 | Jenkins et al. |
| 6,690,005 B2 | 2/2004 | Jenkins et al. |
| 6,915,919 B2 * | 7/2005 | Casterlin ..................... 215/247 |

* cited by examiner

DEVICE FOR TESTING SURFACES OF ARTICLES FOR TRACES OF EXPLOSIVES AND/OR DRUGS

This application claims priority on U.S. Provisional Patent Appl. No. 60/462,559, filed Apr. 10, 2003.

BACKGROUND OF THE INVENTION

1. Field of the Invention

The invention relates to an apparatus for testing for the presence of trace amounts of a contraband material on the surface of an object.

2. Description of the Related Art

Terrorism risks continue to increase at transportation facilities, government buildings, banks, restaurants, hotels and other locations where there is a significant flow of pedestrian or vehicular traffic.

Airlines now routinely screen passengers and employees for explosives. Screening typically is carried out in several stages. For example, all passages are required to pass through a metal detector and all baggage is required to pass through an X-ray apparatus. However, a plastic explosive device could be concealed on a person or in a piece of luggage in a manner that might not be detected by a conventional metal detector or an X-ray apparatus. Even a small amount of a plastic explosive can cause sufficient damage to bring down an aircraft.

Most airports now include apparatus for detecting trace amounts of explosives. These devices operate on the principle that small amounts of the explosive materials will be transferred to the body, clothing and luggage of people who had handled the explosive. Some detectors employ small flexible fabric-like traps that can be wiped across a package or piece of luggage. The trap removes residue from the surface of the package or luggage. The trap then is placed in an apparatus, such as an ion trap mobility spectrometer, that tests the residue on the trap for trace amounts of explosive materials. A device of this type is disclosed in U.S. Pat. No. 5,491,337 and is marketed by the GE Ion Track. These devices typically are employed in proximity to the metal detectors, and security personnel will perform screening on some of the passengers based on a random sampling or based on a determination that the passenger has met certain criteria for enhanced screening.

The ion trap mobility spectrometer disclosed in U.S. Pat. No. 5,491,337 also can operate in a mode for detecting trace amounts of narcotics. Narcotics are illegal and insidious. Furthermore, it is known that many terrorists organizations fund their terrorism through the lucrative sale of narcotics.

The above-described ion trap mobility spectrometer and similar devices have been accepted at airports in view of the notorious efforts of terrorist groups to attack commercial airliners. The above-described detectors have not been accepted widely at other potential targets of terrorism, including train stations, bus terminals, government buildings and the like. The screening of personnel entering train stations, bus depots, government buildings and such by the above-described detection devices would significantly slow the flow of people into and through such buildings and would impose a significant cost penalty on the operators of such facilities.

Only a fraction of airline passengers have their baggage checked for trace amounts of explosives or narcotics using the available ion trap mobility spectrometers and similar devices. Efforts to use such devices to check all bags for trace amounts of explosives or narcotics would impose greater time and cost penalties on the airline industry. Additionally, explosive detectors typically are used only on luggage and other parcels. An apparatus of this type would not identify plastic explosives worn by a passenger who had no carry-on luggage.

U.S. Pat. No. 6,073,499 discloses a walk-through detector. The detector shown in U.S. Pat. No. 6,073,499 operates under the principle that a boundary layer of air adjacent to a person is heated by the person. This heated air adjacent a person is less dense than air further from the person. Less dense air rises. Accordingly, a thermal plume of air flows up adjacent to a person. Minute particles, including particles of explosives or narcotics, will be entrained in this thermal plume of air and will flow upwardly from a person. The walk-through detector disclosed in U.S. Pat. No. 6,073,499 employs an ion mobility spectrometer or ion trap mobility spectrometer to detect microscopic particles of interest that are likely to be entrained in the thermal plume of air flowing upwardly adjacent to a person who walks through and pauses briefly in the detector. The walk-through detector disclosed in U.S. Pat. No. 6,073,499 is very effective for detecting whether a person is carrying explosives or narcotics and whether the person has recently handled explosives or narcotics.

A person who had handled explosives or narcotics is likely to have microscopic residue of the explosive or narcotic materials on his or her fingers, and trace amounts of the explosive or narcotic will be transferred to objects that are handled by the person. For example, it has been assumed that residue of such contraband will be transferred from the fingers to an airline ticket, a boarding pass or an identification card. Hence, the contraband conceivably could be detected on the ticket, pass or card. Efforts have been made to develop a detector that identifies particles of interest on such a card-like object. One such effort used a fabric-like trap, similar to those used to wipe down luggage. The trap was mounted on a heated metal drum that would be rotated against a surface of the card-like object being tested. These efforts have not proved to be commercially successful because of the potential for damage to the ticket or boarding pass due to heat generated by the detector. The trap could be cooled between tests, but such cooling would add significantly to the cycle time. Additionally the fabric traps were found to soil quickly and hence required frequent changing.

In view of the above, it is an object of the invention to provide an apparatus for testing the surfaces of substantially planar sheet-like materials for the presence of explosives, drugs or other substances of interest.

SUMMARY OF THE INVENTION

The subject invention is directed to a detector with means for detecting explosives, narcotics or other substances of interest. The means for detecting preferably is an ion trap mobility spectrometer, such as the detector disclosed in U.S. Pat. No. 5,491,337, the disclosure of which is incorporated herein by reference. A product of this type is marketed by GE Ion Track under the trademark ITEMIZER 3®. The detector also could be an ion mobility spectrometer, such as the type disclosed in U.S. Pat. No. 5,200,614. Other means for detecting trace amounts of explosives, narcotics or other volatile substances can be employed as the detector in the apparatus of the subject invention.

The detector includes a sampling apparatus with a housing that has a slot for receiving the edge of a thin planar material. For example, the slot may be dimensioned for slidably receiving a passenger boarding pass, ticket, credit card, driver's license, employee ID card, passport or the like. For convenience, these thin objects will be referred to collectively as cards.

The card sampling apparatus includes at least one wiper disposed in the housing and in proximity to the slot. The wiper is dimensioned and configured for wiping across a surface of the card as the card is slid through the slot. The wiping interaction between the card and the wiper is effective for removing materials that may have been deposited on the card and that may be of interest. Two wipers preferably are disposed and configured to engage opposite surfaces of the card so that material is effectively scraped or wiped from both opposed surfaces of the card. The wipers preferably are flexible and preferably are formed from a thin metallic material.

The card sampling apparatus includes a switch and/or sensor that is operative to sense that the card has passed completely through the slot. The switch or sensor is operatively connected to an electromechanical device, such as a solenoid, that closes a chamber around the wiper after the card has passed through the slot. The wiper then is heated sufficiently to vaporize and desorb the sampled material on the wiper. The heating may be achieved by applying a voltage across the wiper and thus causing the wiper to heat to approximately 240° C. An airflow then is generated to transfer the desorbed sampled material from the chamber and into the above-described detecting means for analysis. The passage for generating the airflow preferably is heated for delivering air from the chamber at an elevated temperature. The chamber around the wiper preferably remains closed during the analysis.

The apparatus may further include means for displaying the results of the analysis. The displaying means may include a monitor, a printer and/or an audible signal generator.

The apparatus operates the solenoid or other electromechanical apparatus for opening the chamber upon completion of the analysis and for placing the apparatus in a condition for a subsequent sampling.

The apparatus of the subject invention offers several significant advantages. First, the apparatus does not require the time consuming and labor intensive task of rubbing the filter or trap across a surface to be tested, mounting a fabric-like trap or filter into a detector and then waiting for the test results before the tested luggage or parcel can be returned to the customer.

The apparatus also has a desirably short cycle time, preferably in the range of 3-5 seconds. This short cycle time is partly attributable to the use of the thin metallic wiper that can be heated very quickly and then cooled very quickly and partly due to the heating of the air drawn from the chamber. Additionally, the wiper functions to collect and concentrate a sample at the leading edge of the wiper. In contrast, known devices that employ fabric-like traps or filters spread a sample out over the surface. Hence, vaporization of a sample and desorbtion from the edges of the wipers is faster and more complete.

DETAILED DESCRIPTION OF THE PREFERRED EMBODIMENTS

Figure 1:
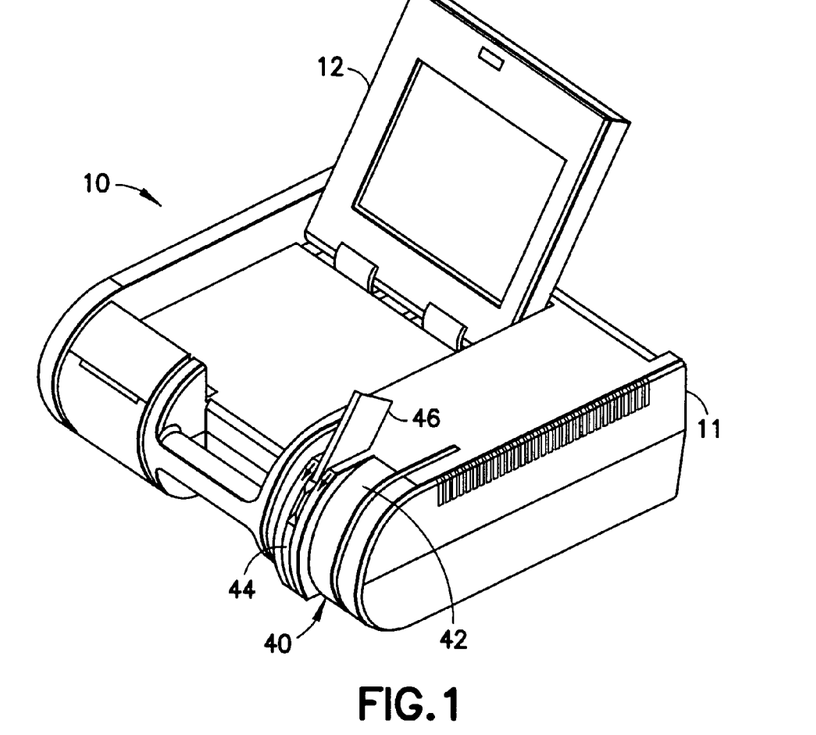
FIG. 1 is a perspective view of a detector that incorporates the apparatus of the subject invention.

A detector according to the invention is identified generally by the numeral 10 in FIG. 1. The detector 10 includes an outer housing 11 and a flat panel display monitor 12 such as an LCD monitor. An ion trap mobility spectrometer (ITMS) is disposed within the housing 11 and is illustrated schematically in FIG. 2.

Figure 2:
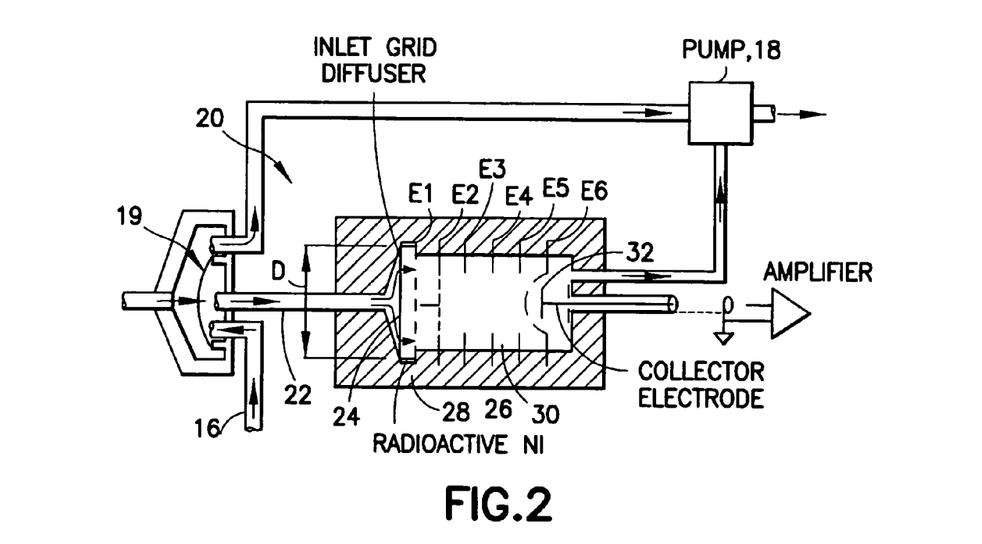
FIG. 2 is a schematic view of an ion trap mobility spectrometer of the detector shown in FIG. 1
Figure 3:
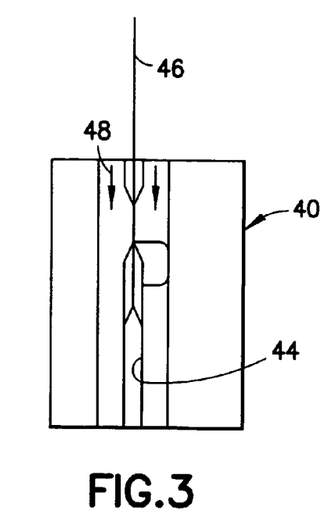
FIG. 3 is a front elevational view of the card sampling apparatus separated from the detector.
Figure 4:
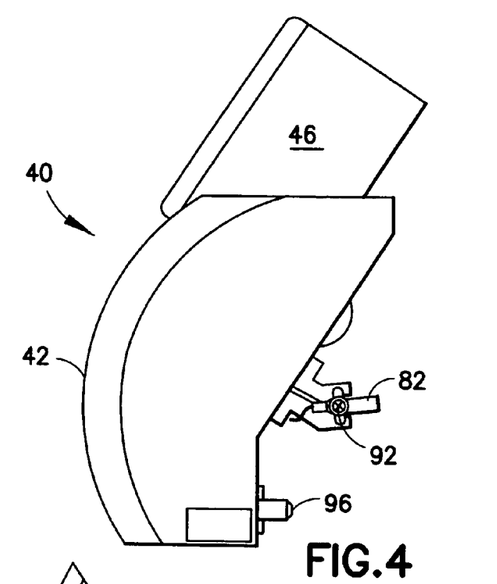
FIG. 4 is a side elevational view of the apparatus.

The ITMS of FIG. 2 comprises a cylindrical detector 20 having an inlet 22 at one end for receiving sample air of interest borne by a carrier gas which that has been doped with a low concentration vapor (typically a few parts per million) employed as a charge transfer mediator. More particularly, the inlet 22 communicates with a source of sample air of interest 14 and a supply of carrier gas and dopant 16 with flows of gases to the inlet 22 being enabled by a flow generator such as a pump illustrated schematically and identified by the numeral 18 in FIG. 2. A heated membrane 19 formed from a microporous refractory material or from dimethyl silicone is disposed near the inlet 22 and in communication with the source of the sample of air 14 for blocking passage of at least selected constituents of the air and for enabling passage of other constituents of the air, including the constituents of interest. The sample air, carrier gas, and dopant molecules pass through the inlet 22 and are spread by a diffuser 24 into an ionization chamber 26. The ionization chamber 26 is in the form of a shallow cylinder with a diameter D, length L, and cylindrical wall 28 of a radioactive material, e.g., nickel$^{63}$ or tritium, which emits beta particles. Inlet 22 communicates with one end of the ionization chamber 26. A grid electrode $E_1$ is provided at the end opposite the inlet 22, and is normally maintained at the same potential as the inlet end and the walls of the ionization chamber 26. Thus a largely field-free space is provided in which electrons and ion charges build up and interact with the sample molecules under bombardment by the beta-particles from the radioactive walls. Beyond the ionization chamber 26, the ionized sample gases pass through open electrode $E_1$ and into an ion drift region 30 having several field-defining electrodes $E_2$-$E_n$. A collector electrode or plate 32 is disposed at the end of the drift region 30 for receiving the ion samples reaching that end.

Periodically a field is established across the ionization region 26, by creating a potential difference between the grid electrode $E_1$ and the inlet diffuser 24 and radioactive source 28, for about 0.1-0.2 mS, to sweep the ions through the open grid $E_1$ into the drift region 30 with the assistance of the switching of the field between electrodes $E_1$ and $E_2$. The ions in the drift region 30 experience a constant electric field, maintained by the annular electrodes $E_2$-$E_n$, impelling them along the region and down toward the collector electrode 32. The electrode 32 detects the arriving charge, and produces signals that are amplified and analyzed through their spectra in the spectrometer. The gases exit through an outlet in the wall next to the electrode 32. After about 0.2 mS the field across the ionization region 26 is again reduced to zero and the ion population is again allowed to build up in the chamber 26 preparatory to the imposition of the next field. The polarity of the fields is chosen on the basis of whether the detector is operated in a negative or positive ion mode. When detecting explosives, a negative ion mode is usually appropriate, but when detecting narcotic samples positive ion mode is preferred.

The card sampling apparatus of the detector 10 is identified generally by the numeral 40 in FIGS. 1 and 3-15. The card sampling apparatus 40 includes a housing 42 with a slot 44. The slot 44 has a wide top and a narrow intermediate section. The wide top of the slot 44 facilitates the guided entry of a card 46 into the slot 44. The slot 44 defines a depth sufficient to accommodate a major portion of the width of the card 46. Arrows 48 are embossed or imprinted prominently on the housing 42 near the slot 44 to indicate the direction for moving the card 46 through the slot 44. The card 46 is depicted to resemble a credit card, an identification card or a driver's license. However, the apparatus 40 can be used with any other thin object, such as a passenger ticket, a boarding pass, a theater ticket or the like.

Figure 9:
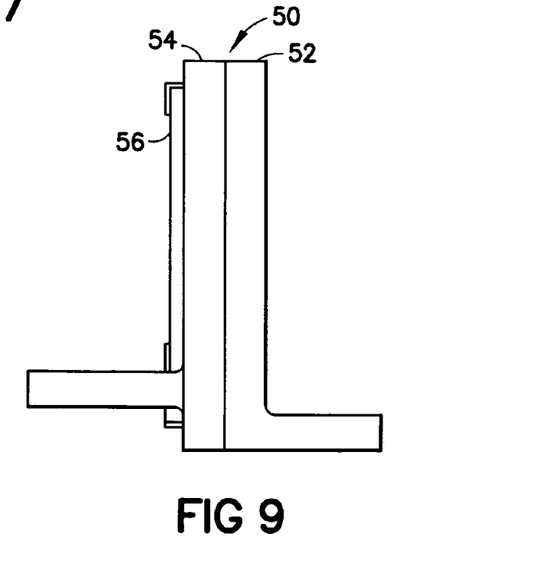
FIG. 9 is an elevational view similar to FIG. 8, but showing the enclosure in the closed position.
Figure 10:
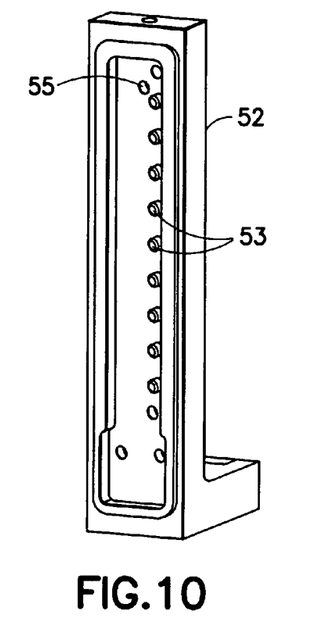
FIG. 10 is a perspective view of the stationary shell of the enclosure.
Figure 11:
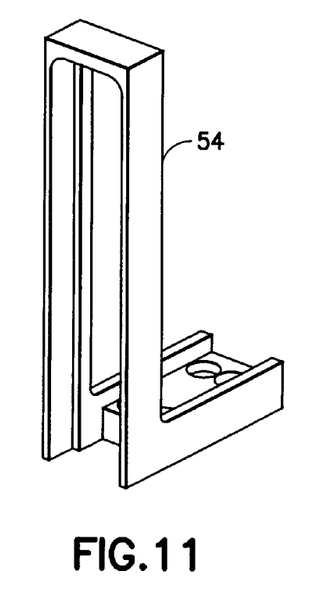
FIG. 11 is a perspective view of the movable shell of the enclosure.

The card sampling apparatus 40 includes an enclosure identified generally by the numeral 50 in FIGS. 6-9. The enclosure 50 includes a stationary shell 52 and a movable shell 54. The stationary shell 52 is formed with a linear array of protrusions 53 and with an air passage 55, as shown in FIG. 10. The stationary shell 52 is mounted fixedly in the housing 42. The movable shell 54 is shown in FIG. 11, and is mountable to a solenoid for selective movement toward and away from the stationary shell 52. More particularly, the movable shell 54 is spaced slightly from the stationary shell 52 in the open position shown in FIG. 8, but is engaged sealingly with the stationary shell 52 in the closed condition shown in FIG. 9.

Figure 12:
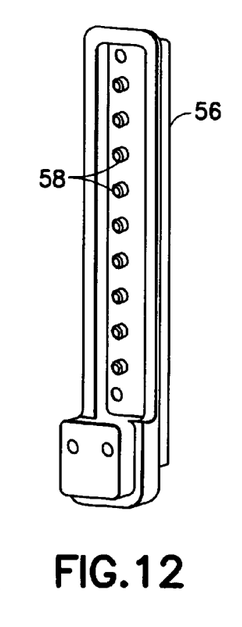
FIG. 12 is a perspective view of the wiper support.

The card sampling apparatus further includes a wiper support 56 as shown in FIG. 12. The wiper support 56 is mounted to the stationary shell 52. The wiper support 56 includes an elongate recess with a linear array of protrusions 58 substantially identical to the protrusions 53 on the stationary shell 52.

Figure 13:
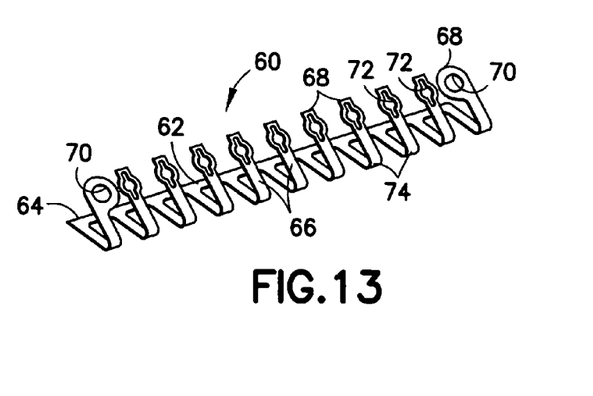
FIG. 13 is a perspective view of the wiper.
Figure 14:
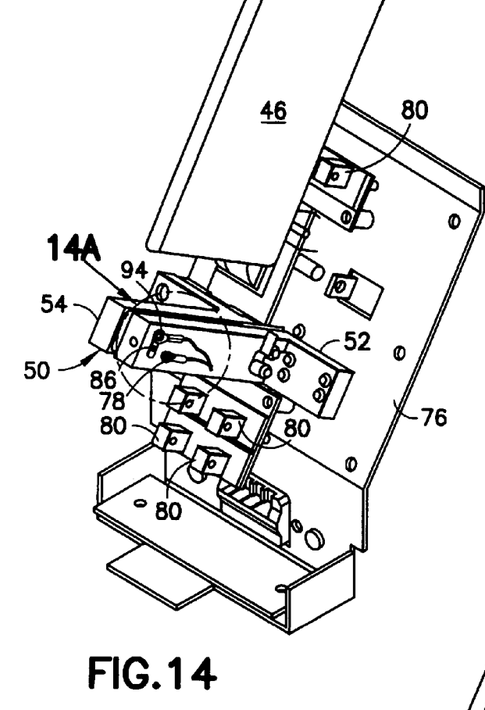
FIGS. 14 and 14A are perspective views of the apparatus with the outer housing removed.
Figure 14A:
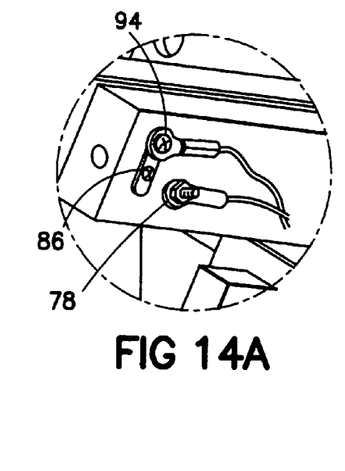
Figure 15:
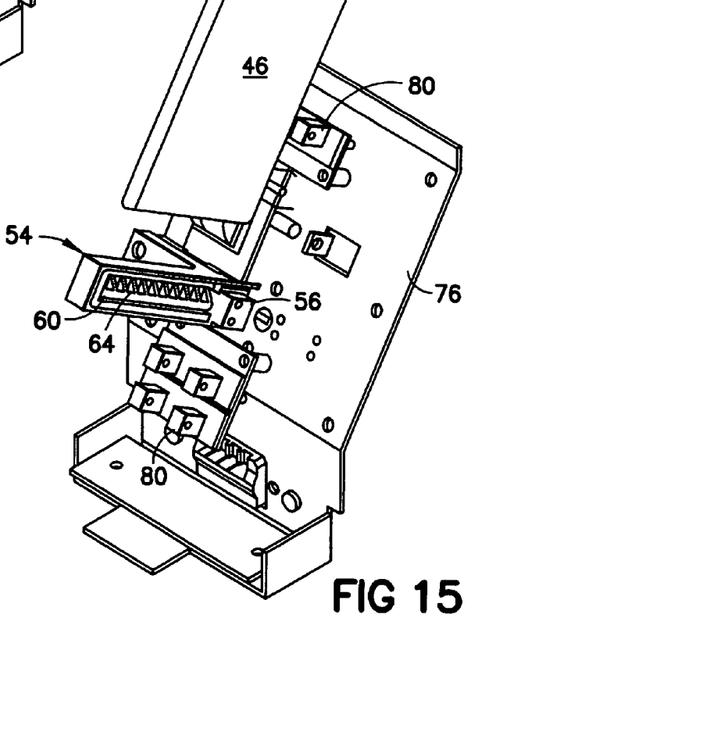
FIG. 15 is a perspective view similar to FIG. 14, but having one enclosure and one wiper removed.

The card sampling apparatus 40 further includes two substantially identical wipers 60, as shown in FIG. 13. A first of the first wipers 60 is mounted to the stationary shell 52 and a second of the wipers 60 is mounted to the wiper support 56, which in turn is mounted to the stationary shell 52. Each wiper 60 is formed from a spring tempered electrically conductive material, such as stainless steel sheet or foil, with a thickness of about 0.002-0.004 inch, and preferably about 0.003 inch. Each wiper 60 has a wiping blade 62 which terminates in a substantially linear wiping edge 64. Thin parallel spring arms 66 extend perpendicularly from the wiping blade 62. The spring arms 66 are disposed and dimensioned such that the distance between adjacent arms 66 exceeds the width of each arm 66. Thus, each wiper 60 has a very low thermal mass, and can heat and cool very quickly. Each spring arm 66 has a mounting end 68 remote from the wiping blade 62. The spring arms 66 at the ends of the wipers 60 have large apertures 70 in the mounting end 68 for receiving screws to mount the respective wiper 60 to the stationary shell 52 or the wiper support 56. All other spring arms 66 have smaller crenulated apertures 72 for force fit engagement onto the protrusions 53 on the stationary shell 52 or the protrusions 58 on the wiper support 56. The spring arms 66 each include a bend 74 between the blade 62 and the mounting ends 68.

A first of the wipers 60 is mounted to the stationary shell 52 by passing screws through the large apertures 70 and into threaded holes in stationary shell 52 and by forcing the small crenulated apertures 72 onto the protrusions 53. A second of the wipers 60 is mounted to the wiper support 56 in a similar manner. The wiper support 56 then is mounted to the stationary shell 52 by screws. As a result, the opposed wipers 60 are juxtaposed so that the wiping edges 64 are parallel and preloaded against one another. In the illustrated embodiment, the wiping blades 62 and adjacent parts of the spring arms 66 of the opposed wipers 60 define a V-shape that points in the direction of movement of the card.

The subassembly of the stationary shell 52 the wiper support 56 and the wipers 60 are mounted to a support 76 in the card sampling apparatus 40 so that the abutting edges 64 of the wipers 60 are aligned perpendicular to the direction of movement of the card 46 through the slot 44. Additionally, V-shape defined by the wipers 60 points in the card insertion direction. The movable shell 54 then is mounted to oppose the stationary shell 52. In other embodiments, the wipers may define oppositely directed $\Omega$ shapes so that the card can be slid in either direction.

The card sampling apparatus 40 further includes terminals 78 on the stationary shell 52 and on the wiper support 56. The terminals 78 are connected to wires (not shown) and are operative for delivering an electric current to the wipers 60 for rapidly heating the wipers 60.

Figure 5:
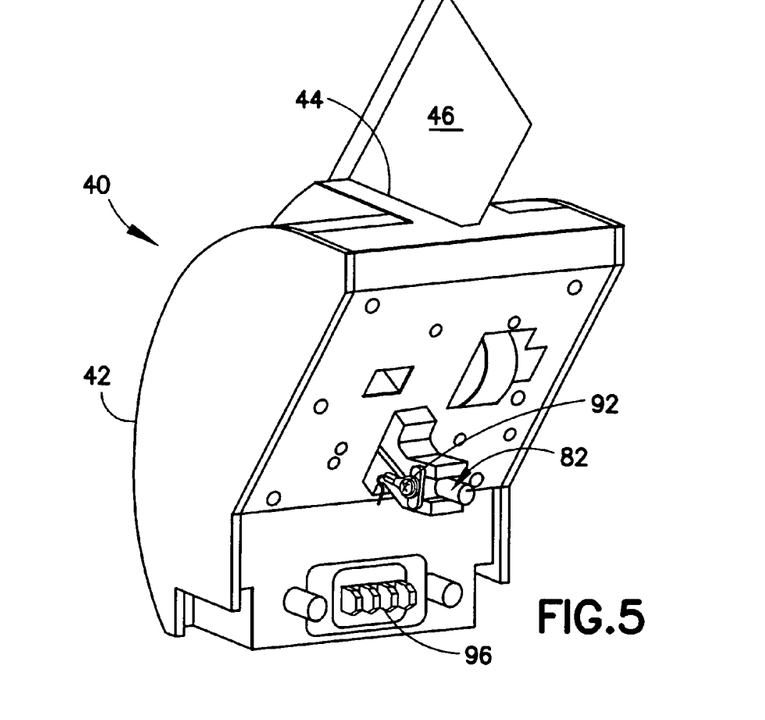
FIG. 5 is a rear perspective view of the apparatus.
Figure 6:
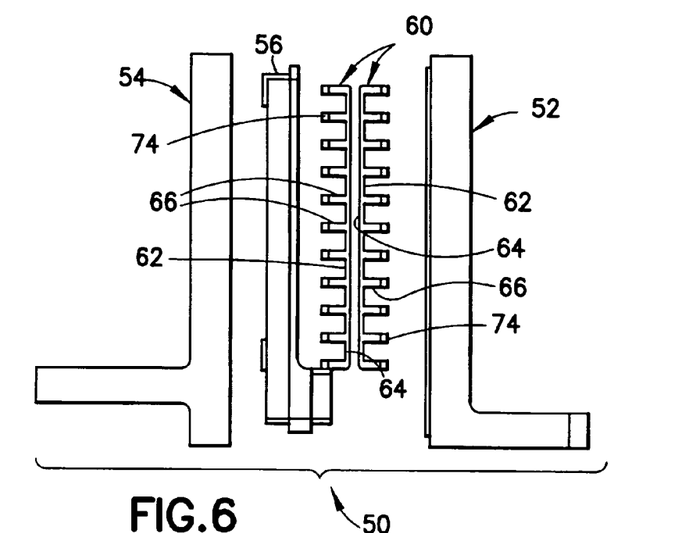
FIG. 6 is an exploded elevational view of the apparatus with the outer housing removed.
Figure 7:
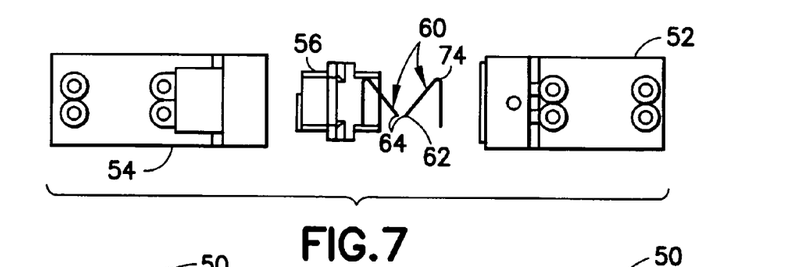
FIG. 7 is an exploded top plan view of the apparatus shown in FIG. 6.
Figure 8:
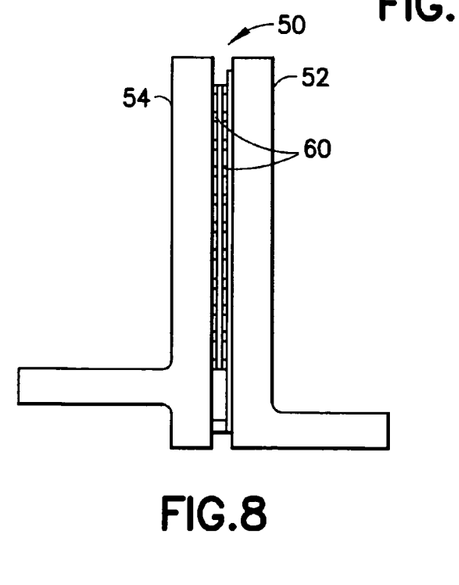
FIG. 8 is an elevational view of the portion of the apparatus shown in FIGS. 6 and 7 in a fully assembled condition and with the enclosure in an open ready-to-use position.
Figure 16:
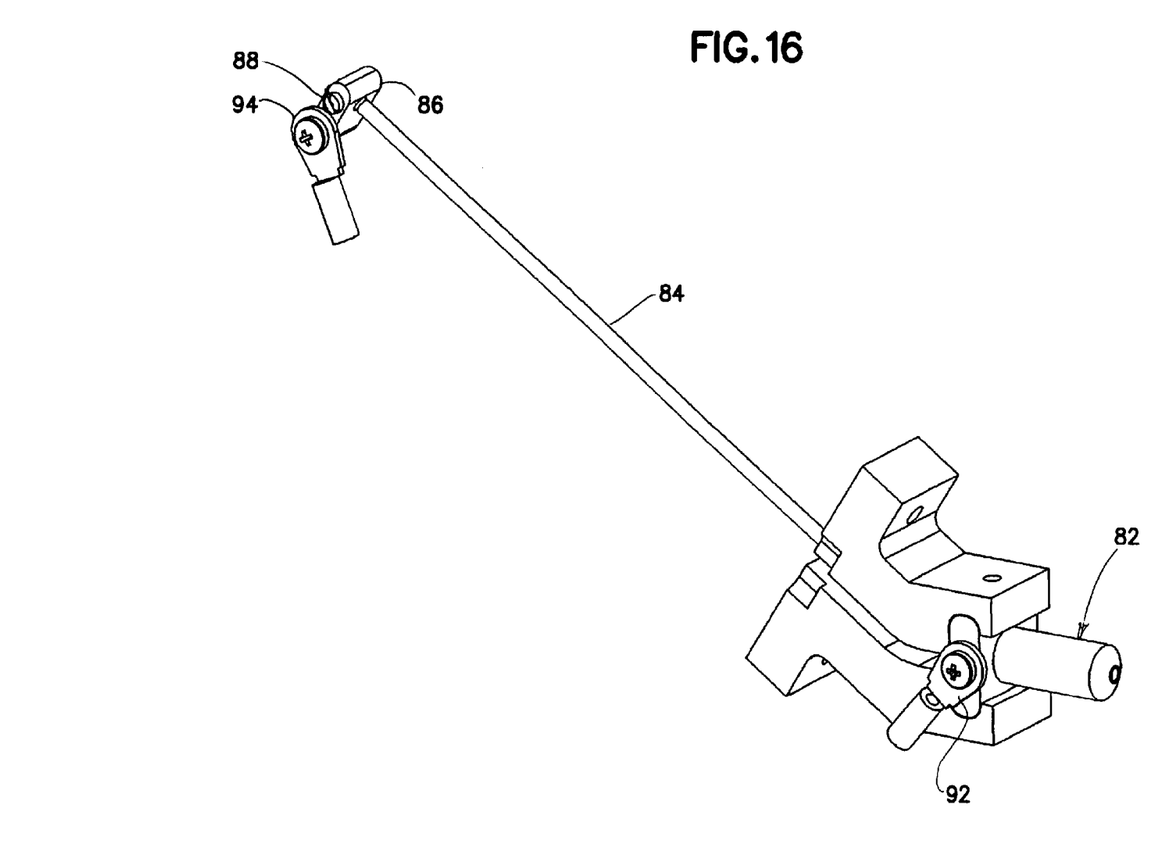
FIGS. 16 and 17 are perspective views showing structure for delivering heated air to the ion trap mobility spectrometer.
Figure 17:
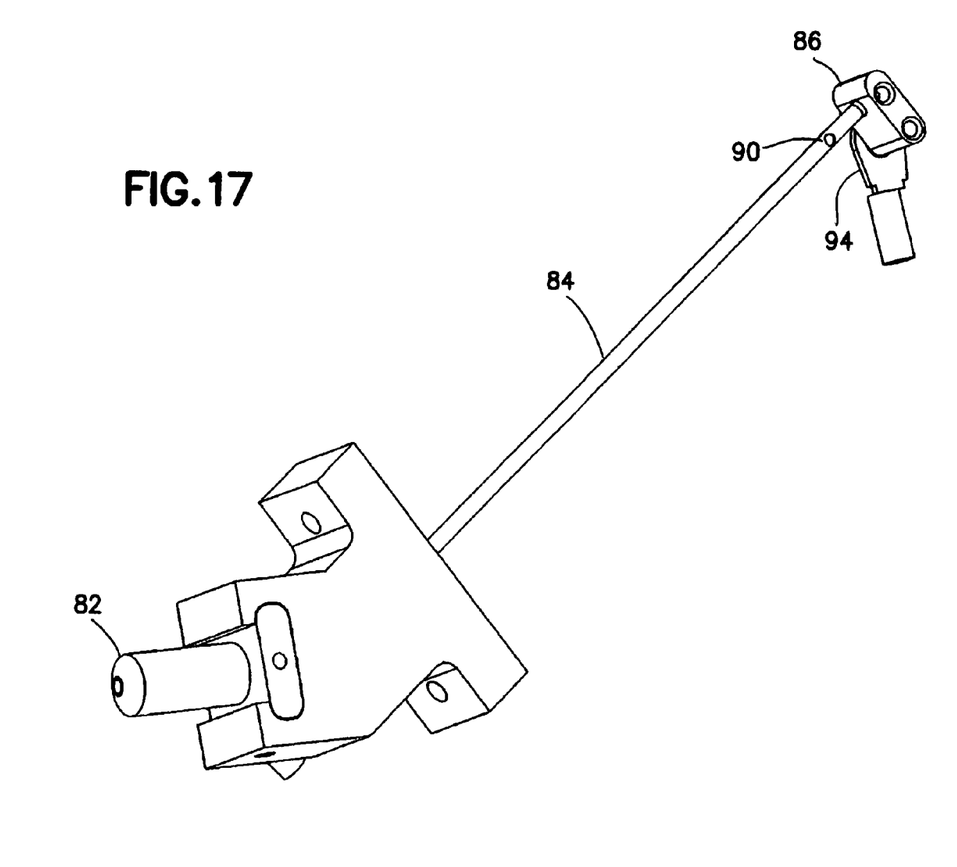

The card sampling apparatus 40 further includes sensors 80 for detecting when a card 46 has passed through the slot 44. Additionally, the card sampling apparatus 40 also includes an outlet 82 as shown in FIG. 5. A stainless steel tube 84 extends between the outlet 82 and the enclosure 50. The end of the tube 84 remote from the outlet 82 passes into the stationary shell 52 and is capped by a conductive cap 86, as shown in FIGS. 16 and 17. The cap 86 is held in place by a set screw 88. The tube 84 includes a transverse hole 90 as shown in FIG. 17. The hole 90 communicates with the air passage 55 in the stationary shell 52, and hence lets air flow from the enclosure 50 to the tube 84 and then to the outlet 82 so that the desorbed sample can be delivered between the enclosure 50 and the inlet 22 of the ITMS shown in FIG. 2. A terminal 92 is connected to the outlet 82, and a terminal 94 is connected to the cap 86. Wires connected to the terminals 92 and 94 apply a voltage that enables the stainless steel tube 84 to be heated to about 160° C. for heating the air flowing between the enclosure 50 and the outlet 82. Furthermore, the card sampling apparatus 40 includes an electrical connector 96 for connecting the card sampling apparatus 40 to a controller (not shown) mounted in the detector 10 for controlling the closing of the enclosure 50 after passage of the card 46 and for controlling the heating of the wipers 60 when the enclosure 50 is closed.

The detector 10 is employed by merely swiping a card 46 through the slot 44 in the card sampling apparatus 40. The movement of the card 46 through the slot 44 causes the card 46 to move between the wiping edges 64 of the wipers 60. Hence, the spring arms 66 deflect about the respective bends 74. The spring tempered metallic material of the wipers 60 will cause the wiping blades 62 to exert a biasing force against opposite side surfaces of the card 46. The spaces between the spring arms 66 are sufficiently large and the spring arms 66 are sufficiently thin to require only a minor force to pass the card 46 between the biased wiping blades 62 of the wipers 60. However, the resiliency of the spring metal will exert a sufficient force for keeping the wiping edges 64 in contact with the opposed side surfaces of the card 46.

The sensors 80 will sense when the card 46 has completed passing through the slot 44. Hence, the signal generated by the sensors 80 will cause the controller to move the movable shell 54 toward the stationary shell 52 and into the closed position around the wipers 60, as shown in FIG. 9. Current then will be applied to the terminals 78 for heating the wipers 60 to a temperature of approximately 240° C. This heating can be carried out very quickly in view of the relatively small thickness (e.g. 0.003 inch) of the wipers 60. Additionally the spaces between the spring arms 66 reduce the thermal mass of metal material that must be heated, and hence contribute to very rapid heating of the wipers 60. The heating vaporizes and desorbs material collected on the wiping edges 64 of the wipers 60. Simultaneously, the ITMS illustrated in FIG. 2 is actuated to draw air and potential vaporized particles of interest through the air passage 55 and into the inlet 22, both of which are heated. The ITMS then is operated in the manner described above and in U.S. Pat. No. 5,491,337 to identify any minute amounts of substances of interest that will have been wiped from the card 46 by the wipers 60. The results of the analysis will be displayed on the monitor 12. The cycle time between the initial swiping of the card 46 through the slot 44 to the display of the test results on the monitor 12 is likely to be approximately 3-4 seconds.

The low thermal mass of the wipers 62 and 64 ensures that the wipers will cool quickly after termination of the electric current and the opening of the enclosure 50. Hence the wipers will be at a sufficiently low temperature to prevent damage to a card 46 during a subsequent cycle.

The rapid cycle time and high efficiency of the detector 10 is partly attributable to the concentration of sample material on the edges 64 of the wipers 60. More particularly, conventional detectors employ a soft fabric-like filter or trap material, and samples are collected across a relatively large surface area of the material. Subsequent desorbtion or vaporization of the sample is slower and less complete. In contrast, the concentration of the samples on the thin edges 64 of the wiper 60 is well suited to rapid desorbtion/vaporization and achieves a very high efficiency and accuracy.

The invention has been described with respect to a preferred embodiment. However, variations will be apparent to a person skilled in the art after having read the subject disclosure. For example, the invention has been depicted with respect to a stand-alone dedicated apparatus for detecting the presence of substances of interest on the card. However, the apparatus can be incorporated into a multifunction device. For example, the apparatus can be incorporated into an e-ticket machine common at airport terminals or into a boarding pass scanning machine, common at many boarding gates. Thus, any apparatus that receives and processes a card for some other purpose can be adapted to include the apparatus of the subject invention. Additionally, the apparatus has been described as being used with an ion trap mobility spectrometer. However, other devices are known for identifying particular substances of interest, and any such devices can be employed with the subject invention.

What is claimed is:

1. An apparatus for collecting samples of interest from a card, the apparatus comprising a housing formed with a slot dimensioned for slidably receiving the card, at least one wiper disposed in the housing substantially adjacent the slot for biased engagement against the card slid through the slot and an enclosure formed separately from the wiper, at least a portion of the enclosure selectively movable for enclosing the wiper after the card has been slid through the slot and for subsequently opening to permit another card to be slid through the slot.

2. The apparatus of claim 1, wherein the slot is configured to define a direction of movement for sliding the card through the slot, the wiper having a wiping blade with a longitudinal direction aligned substantially orthogonal to the direction of movement.

3. The apparatus of claim 1, wherein the at least one wiper comprises two wipers substantially juxtaposed to one another and projecting into the slot from opposite sides of the slot so that a card slidably received in the slot passes between the juxtaposed wipers, each said wiper having a blade, the blades being disposed respectively for contact with opposite sides of the card, the blades being resiliently deflectable away from one another in response to forces exerted by the card.

4. The apparatus of claim 1, wherein the wiper is formed from an electrically conductive material.

5. The apparatus of claim 4, wherein the electrically conductive material is a metallic foil having a thickness of between about 0.002-0.004 inch.

6. The apparatus of claim 4, wherein the wiper has a blade for contacting the card and a plurality of spring arms extending from the blade for supporting the blade in the housing, the spring arms of the wiper being spaced sufficiently from one another for reducing thermal mass of the wiper and facilitating deflection.

7. The apparatus of claim 1, further comprising connections for applying an electric current to the wiper for selectively heating the wiper.

8. The apparatus of claim 1, further comprising a sensor for sensing movement of the card through the slot.

9. An apparatus for collecting samples from surfaces of a card, the apparatus comprising first and second wipers formed from an electrically conductive material, each said wiper having a blade with a wiping area, the wiping areas being disposed for contacting opposite surfaces of the card upon insertion of the card between the wipers, an enclosure for selectively enclosing said wipers, and a heater for heating the wipers sufficiently for vaporizing samples of material collected on said wiping edges.

10. The apparatus of claim 9, wherein the blades of the wipers are oriented to define an acute angle to a card disposed between the wipers.

11. The apparatus of claim 9, wherein the wiping areas of the wipers are preloaded against one another.

12. The apparatus of claim 9, wherein the enclosure for enclosing said wipers includes first and second shells, at least one of said shells being movable toward and away from the other of the shells for selectively enclosing the wipers, the apparatus further comprising a detector communicating with said enclosure and operative for detecting substances of interest collected on said wipers from said card.

13. The apparatus of claim 12, wherein the detector is an ion trap mobility spectrometer.

14. An apparatus for testing for substances of interest on surfaces of a card, said apparatus comprising;
    a housing having a slot formed therein for slidably receiving said card; first and second metallic wipers disposed in said apparatus and in proximity to said slot, said first and second metallic wipers being formed respectively with first and second resiliently deflectable wiper blades biased toward one another, said blades having wiping areas disposed relative to one another for contacting opposite surfaces of said card upon moving said card through said slot;

an enclosure selectively movable from an open position where said wipers are exposed for access at said slot and a closed position where said wipers are substantially enclosed;

an electric heater for heating said wipers when said enclosure is in said closed position; and a detector communicating with said enclosure for testing for substances of interest collected on said blades of said wipers.

15. The apparatus of claim 14, further comprising a sensor for sensing passage of said card through said slot, said sensor generating a signal for closing said enclosure when said sensor means senses the passage of said card.

16. The apparatus of claim 14, wherein each said wiper has a plurality of spring arms extending from the blade of the respective wiper, said spring arms being spaced apart for reducing thermal mass and increasing flexibility.

17. The apparatus of claim 14, wherein the wipers are formed from a stainless steel having a thickness of between approximately 0.002-0.004 inch.

18. A method for testing for substances of interest, said method comprising:

receiving a substantially flat card from a suspect;

passing the card against at least one resiliently deflectable metallic wiper mounted in a testing apparatus so that said wiper removes substances from said card;

separating the card from the wiper; enclosing the wiper in an enclosure in the testing apparatus;

heating the wiper in the enclosure sufficiently for desorbing substances removed from said card and onto said wiper;

placing said wiper in communication with a detector; and testing the desorbed substances for the presence of a substance of interest.

19. The method of claim 18, wherein the step of heating comprises heating the wiper to a temperature of approximately 240° C.

20. The method of claim 18, further comprising the step of opening the enclosure after the testing step.

21. The method of claim 18, wherein the at least one resiliently deflectable metallic wiper comprises at least one pair of opposed resiliently deflectable metallic wipers, and wherein the step of passing the card against a resiliently deflectable metallic wiper comprises passing the card between the opposed resiliently deflectable metallic wipers so that the wipers remove substances from opposite sides of the card, and wherein the step of enclosing the wiper comprises enclosing the pair of wipers.

* * * * *